(12) United States Patent
An et al.

(10) Patent No.: US 8,877,463 B2
(45) Date of Patent: Nov. 4, 2014

(54) RHODANOBACTER GINSENOSIDIMUTANS KCTC22231T-DERIVED GINSENOSIDE GLYCOSIDASE, AND USE THEREOF

(75) Inventors: Dong-Shan An, Daejeon (KR);
Song-Gun Kim, Daejeon (KR);
Sung-Taik Lee, Daejeon (KR);
Wan-Taek Im, Daejeon (KR);
Chang-Hao Cui, Daejeon (KR)

(73) Assignee: Korea Research Institute of Bioscience and Biotechnology, Dajeon (KR)

( * ) Notice: Subject to any disclaimer, the term of this patent is extended or adjusted under 35 U.S.C. 154(b) by 0 days.

(21) Appl. No.: 13/497,042

(22) PCT Filed: Sep. 20, 2010

(86) PCT No.: PCT/KR2010/006502
§ 371 (c)(1),
(2), (4) Date: Apr. 6, 2012

(87) PCT Pub. No.: WO2011/034406
PCT Pub. Date: Mar. 24, 2011

(65) Prior Publication Data
US 2012/0190063 A1    Jul. 26, 2012

(30) Foreign Application Priority Data
Sep. 18, 2009    (KR) .................. 10-2009-0088734

(51) Int. Cl.
| | |
|---|---|
| *C12P 19/56* | (2006.01) |
| *C12N 9/24* | (2006.01) |
| *C12N 1/21* | (2006.01) |
| *C12N 15/56* | (2006.01) |
| *C12N 15/63* | (2006.01) |
| *C12N 15/70* | (2006.01) |
| *C12N 9/42* | (2006.01) |
| *A61K 31/704* | (2006.01) |

(52) U.S. Cl.
CPC .............. *C12P 19/56* (2013.01); *C12N 9/2402* (2013.01); *C12Y 302/01071* (2013.01); *C12Y 302/01075* (2013.01); *C12Y 302/01088* (2013.01); *C12Y 302/01021* (2013.01); *C12N 9/2445* (2013.01); *A61K 31/704* (2013.01)
USPC ........... 435/78; 435/74; 435/200; 435/252.3; 435/252.33; 435/320.1; 435/69.1; 536/23.2

(58) Field of Classification Search
None
See application file for complete search history.

(56) References Cited

U.S. PATENT DOCUMENTS

| | | |
|---|---|---|
| 2004/0028671 A1 | 2/2004 | Jin et al. |
| 2008/0275225 A1 | 11/2008 | Hui et al. |

FOREIGN PATENT DOCUMENTS

KR    1020000062140 A    10/2000

OTHER PUBLICATIONS

GenBank, Accession No. AAF097413,1999, www.ncbi.nlm.nih.gov.*
An et al., Rhodanobacter Ginsenosidimutans sp. nov., isolated from soil of a Ginsing Field in South Korea, International Journal of Systematic and Evolutionary Microbiology, 2009, 59, 691-694.
An, Dong-Shan, Characterization of ginsenoside-converting bacteria isolated from soil of ginsing field, Doctoral Thesis, Nov. 28, 2008, all pages, Republic of Korea.

* cited by examiner

*Primary Examiner* — Rebecca Prouty
*Assistant Examiner* — Todd M Epstein
(74) *Attorney, Agent, or Firm* — Benjamin Aaron Adler

(57) ABSTRACT

The present invention relates to Rhodanobacter ginsenosidimutans KCTC22231T-derived ginsenoside glycosidase and use thereof. The polypeptide has an activity of converting PPD (protopanaxadiol)-type saponins into in vivo absorbable and highly active deglycosylated saponins, by selective hydrolysis of a bond at a particular position of ginsenoside. The present invention also relates an amino acid sequence constituting the polypeptide, a nucleic acid sequence encoding the protein, a recombinant vector comprising the nucleic acid sequence, and a transformant transformed with the vector. The invention further provides a method for preparing Rhodanobacter ginsenosidimutans KCTC22231T-derived ginsenoside glycosidase by culturing the transformant, a method for converting PPD (protopanaxadiol)-type major ginsenoside into a rare ginsenoside that is absorbable in vivo using the protein, and a composition for converting PPD-type saponins into in vivo absorbable saponins, having the protein as an active ingredient.

9 Claims, 11 Drawing Sheets

Figure 1

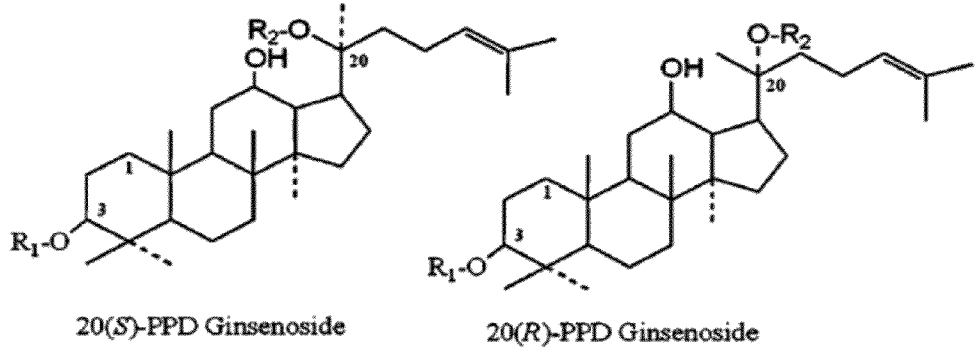

20(S)-PPD Ginsenoside        20(R)-PPD Ginsenoside

| Ginsenoside | R₁ | R₂ |
|---|---|---|
| Rb1 | Glc¹-²Glc- | Glc¹-⁶Glc- (S) |
| Rb2 | Glc¹-²Glc- | Ara(p)¹-⁶Glc- (S) |
| Rb3 | Glc¹-²Glc- | Xyl¹-⁶Glc- (S) |
| Rc | Glc¹-²Glc- | Ara(f)¹-⁶Glc- (S) |
| Rd | Glc¹-²Glc- | Glc- (S) |
| Gypenoside 17 | Glc- | Glc¹-⁶Glc- (S) |
| Compound O | Glc- | Ara(p)¹-⁶Glc- (S) |
| Compound Mc1 | Glc- | Ara(f)¹-⁶Glc- (S) |
| F2 | Glc- | Glc- (S) |
| Gypenoside 75 | H- | Glc¹-⁶Glc- (S) |
| Compound Y | H- | Ara(p)¹-⁶Glc- (S) |
| Compound Mc | H- | Ara(f)¹-⁶Glc- (S) |
| Rg3 | Glc¹-²Glc- | H- (R, S) |
| Rh2 | Glc- | H- (R, S) |
| C-K | H- | Glc- (S) |

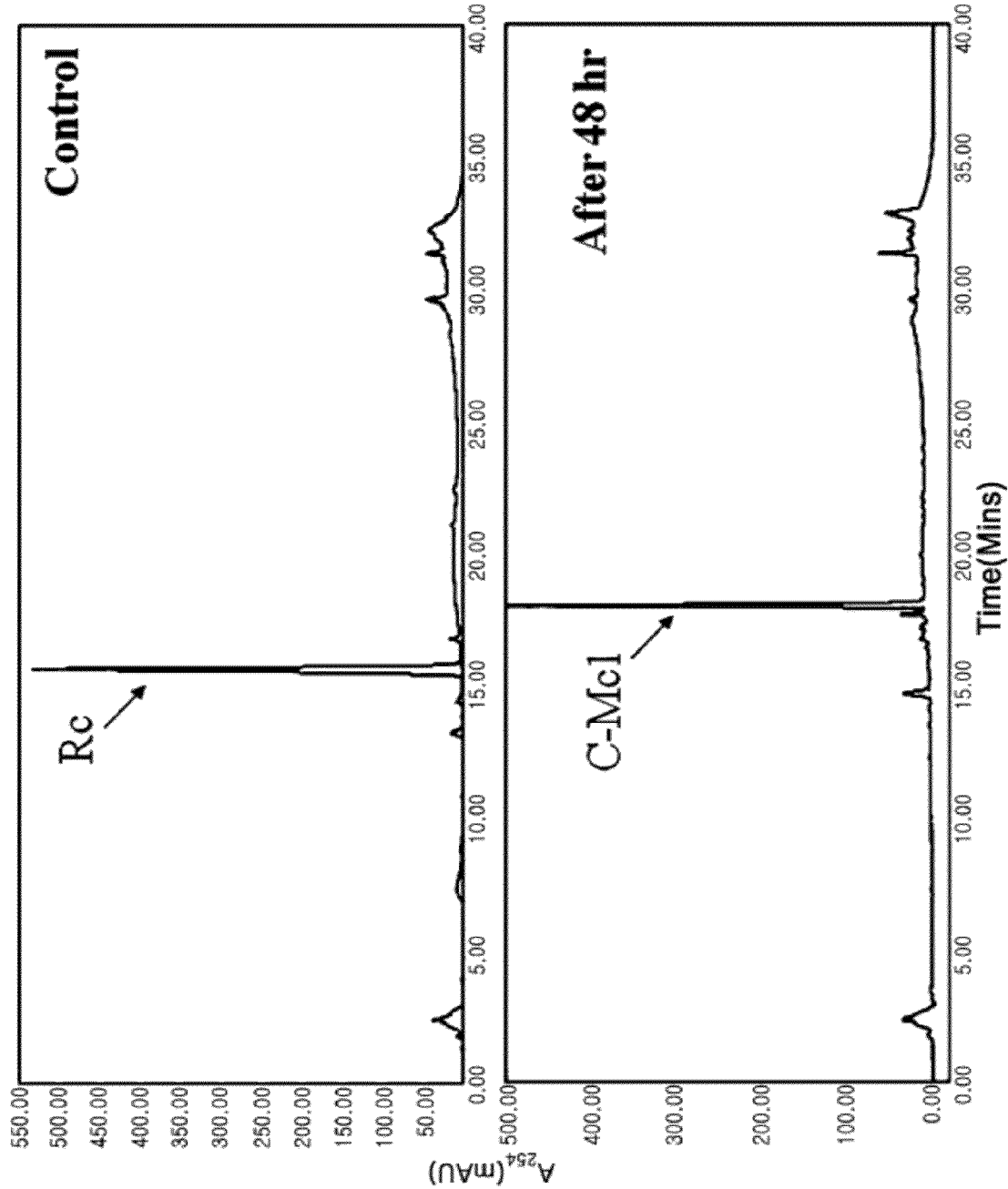

RHODANOBACTER GINSENOSIDIMUTANS KCTC22231T-DERIVED GINSENOSIDE GLYCOSIDASE, AND USE THEREOF

TECHNICAL FIELD

The present invention relates to Rhodanobacter ginsenosidimutans KCTC22231T-derived ginsenoside glycosidase protein and use thereof, and more particularly, to an amino acid sequence constituting the protein, a nucleic acid sequence encoding the protein, a recombinant vector comprising the nucleic acid sequence, a transformant transformed with the vector, a method for preparing Rhodanobacter ginsenosidimutans KCTC22231T-derived ginsenoside glycosidase by culturing the transformant, a method for converting PPD (protopanaxadiol)-type major ginsenosides into in vivo absorbable rare ginsenosides using the protein, and a composition for converting PPD-type saponins into in vivo absorbable saponins, comprising the protein as an active ingredient.

BACKGROUND ART

Saponins, glycosides widely distributed in the plant kingdom, include diverse ring compounds formed by the non-sugar portion thereof. Triterpene saponin is a saponin that is contained in ginseng or red ginseng as a major physiologically active ingredient, and this ginseng saponin is named ginsenoside, which means ginseng glycoside, to specifically distinguish it from other vegetables' saponin based on a different chemical structure.

Ginsenosides are classified into three groups based on their aglycone structure: Protopanaxadiol-type ginsenosides, Protopanaxatriol-type ginsenosides, and Oleanolic acid-type ginsenosides. These three groups are further classified based on the position and number of sugar moieties (aglycones) attached by a glycosidic bond at the C-3, C-6, and C-20 positions of the rings in the chemical structure. The oleanolic acid-type ginsenoside has a pentacyclic backbone and ginsenoside Ro is the only saponin having oleanolic acid as aglycone. To date, more than 40 ginsenosides have been isolated, and most of them are Protopanaxadiol-type ginsenosides. Protopanaxadiol-type ginsenosides include Rb1, Rb2, Rb3, Rc, Rd, Gypenoside XVII, Compound O, Compound Mc1, F2, Compound Y, Compound Mc, Rg3, Rh2, and C-K.

In addition, major ginsenosides account for over 90% of total ginsenoside content, but show a very low in vivo absorption because of their large size. Therefore, in order to increase the efficacy of ginsenoside, it is required that major ginsenosides are converted into rare ginsenosides showing a relatively excellent absorption and efficacy. That is, deglycosylation of major ginsenosides is required to show effective physiological activities in vivo (Tawab et al., 2003; Akao et al., 1998). The major ginsenosides include Rg1, Re, Rb1, Rc, Rb2, or the like, and the rare ginsenosides include F2, Rg3, Rh1, Rh2 and compound K, C-K, Mc, Mc1 or the like.

Among the rare ginsenosides, Mc1 is a ginsenoside that is mainly included in red ginseng in a trace amount, and the compound Mc1 is produced as a metabolite upon intake of diol-type ginsenoside Rc having functions of alleviating pain, accelerating secretion of corticosterone, suppressing hypertrophy of glomerulus, suppressing lipid peroxidation of liver cell, and stimulating the synthesis of bone marrow cell, DNA, RNA, protein, and lipid. Various studies on the pharmaceutical activities of the compound Mc1 have not been made yet, because it is present in a very small amount.

Further, rare ginsenoside F2 has been known as an ingredient having effects of suppressing proliferation of tumor cells and reversing the multi-drug resistance in tumor cells or bacteria (*Korean Journal of Pharmacognosy* 28(1), 35, Jong Hwan Sung et al., 1997). Ginsenoside F2 is found in only small amounts in ginseng. When administered in the body, saponin is finally transformed into compound K via the intermediate metabolite, ginsenoside F2. Therefore, it is very difficult to produce a large amount of ginsenoside F2.

Meanwhile, the known preparation method of ginsenoside F2 is a method of preparing ginsenoside F2 by hydrolysis of a diol-based saponin using an enzyme naringinase or by the decomposition in the rat large intestine after oral administration. However, these methods show very low yields, and it is difficult to produce high-purity ginsenoside F2 due to the production of various secondary metabolites (Koizumi et al., Chem. Pharm. Bull. 30(7):2393, 1982; Karikura et al., Chem. Pharm. Bull.). Even though the mass-production methods thereof have been studied, effective methods have not yet been established.

Further, ginsenoside F2 has been known to have the effects of suppressing the proliferation of tumor cells and reversing multi-drug resistance in tumor cells or bacteria (Korean Journal of Pharmacognosy 28(1), 35, Jong Hwan Sung et al., 1997). It is known that ginseng ginsenosides are metabolized by intestinal flora such as *Prevotella Oris* after they are orally administered, and their metabolite F2 shows pharmaceutical effects. However, the useful F2 is also present in only small amounts in some ginsengs, and thus it is difficult to produce a large amount thereof. In addition, it is difficult to produce only high-purity F2 because of the production of various secondary metabolites during the metabolic process.

For the production of rare ginsenosides present in a small amount, chemical decomposition (De Mayo et al., canad. J. Chem., 43, 2033, 1965), an enzymatic method (Kitagawa et al., Terahedron Letters, 30, 2283, 1974), and glycoside synthesis (Korean Patent No. 10-2005-0007250) have been suggested, but these methods have limitations in mass-production such as 1) requiring many production steps for the production process, 2) loss of desired compounds during processing, 3) use of inedible catalysts, or 4) low yield.

In particular, enzymes such as β-glucosidase, β-L-arabinopyranosidase, β-L-arabinofuranosidase, and β-L-rhamnosidase can be used in the enzymatic method, and there have been many studies on biotransformation of major ginsenosides using these enzymes. However, these methods are also not effective for mass-production, and have a problem in that they require high production costs.

Moreover, not all enzymes of β-glucosidase, β-L-arabinopyranosidase, β-L-arabinofuranosidase, and β-L-rhamnosidase do have the activity of biotransformation of major ginsenosides into rare ginsenosides. For example, the present inventors demonstrated that beta-glucosidase known to be derived from *Arthrobacter chlorophenolicus* A6 has no activity of the biotransformation of ginsenoside. In addition, even though a known enzyme, for example, beta-glucosidase A, is known to have biotransformation activity into Rb1, the activity was not satisfactory.

Korean Patent Application No. 10-1999-0045180 provides a method for preparing ginsenoside Rh2 by degradation of saccharide of PPD-type ginsenoside using saponin alpha-glucosidase. The saponin alpha-glucosidase of the above invention converts ginsenoside Rd into ginsenoside Rh2 via ginsenoside F2. In addition, ginsenoside Rh2 can be produced from ginsenoside Rb1 and Rc. As described in Example 3, however, the saponin alpha-glucosidase should be obtained by removal of bacterial cells from the culture broth of *Aspergillus* in media containing wheat bran and ginseng powder. Thus, the resulting low production yield increases the production cost in mass-production, and loss or the desired product problematically occurs during the production process.

DISCLOSURE

Technical Problem

The present inventors have made many efforts to develop a method for mass-producing minor ginsenosides present in small amounts in plants such as ginseng with high yield. As a result, they obtained a ginsenoside glycosidase gene having biotransformation activity of major ginsenosides into rare ginsenosides using a Rhodanobacter ginsenosidimutans KCTC22231T strain. The present inventors found that a recombinant enzyme expressed by cloning the gene converts major ginsenosides into rare ginsenoside having high physiological activity and in vivo absorption by selective hydrolysis of a particular molecular bond of major ginsenosides, thereby completing the present invention.

Technical Solution

An object of the present invention is to provide a Rhodanobacter ginsenosidimutans KCTC22231T-derived ginsenoside glycosidase protein.

Another object of the present invention is to provide a nucleic acid encoding the protein.

Still another object of the present invention is to provide a recombinant vector comprising the nucleic acid.

Still another object of the present invention is to provide a transformant transformed with the vector.

Still another object of the present invention is to provide a method for preparing Rhodanobacter ginsenosidimutans KCTC22231T-derived ginsenoside glycosidase, comprising the steps of culturing the transformant that is transformed with the vector including the nucleic acid encoding the Rhodanobacter ginsenosidimutans KCTC22231T-derived ginsenoside glycosidase; producing ginsenoside glycosidase from the cultured transformant; and recovering the produced ginsenoside glycosidase.

Still another object of the present invention is to provide a method for converting the PPD-type saponins into in vivo absorbable saponins using Rhodanobacter ginsenosidimutans KCTC22231T-derived ginsenoside glycosidase.

Still another object of the present invention is to provide a composition for converting PPD-type saponins into in vivo absorbable saponins, comprising Rhodanobacter ginsenosidimutans KCTC22231T-derived ginsenoside glycosidase as an active ingredient.

Advantageous Effects

The Rhodanobacter ginsenosidimutans KCTC22231T-derived ginsenoside glycosidase of the present invention shows excellent activity of converting saponins into in vivo absorbable forms, and produces a large amount of rare ginsenosides which are present in trace amounts in nature and thus have limited usage even though their efficacies are demonstrated. In addition, it can be mass-produced by culturing a transformant that is transformed with a recombinant vector including a nucleic acid encoding ginsenoside glycosidase, thereby being industrially applicable.

DESCRIPTION OF DRAWINGS

FIG. 1 shows a variety of PPD (Protopanaxadiol)-type ginsenosides;

FIG. 12 is the result of HPLC showing time course of the bioconversion of Rc_Mc1 using Bgl 3054.

BEST MODE

Figure 2:
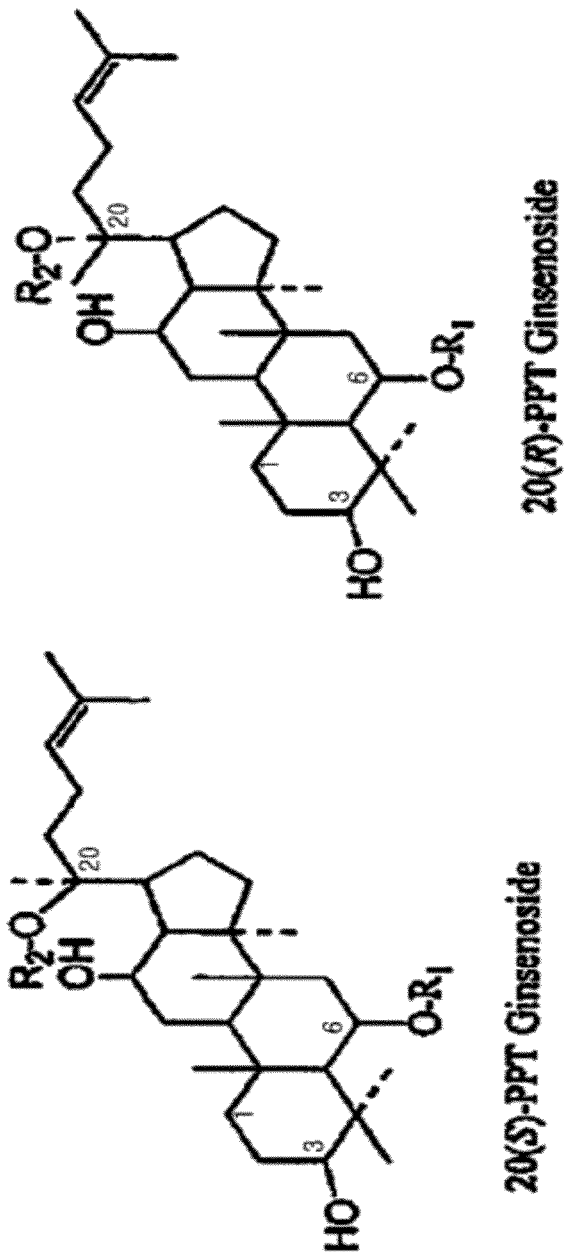
FIG. 2 shows a variety of PPT (Protopanaxatriol)-type ginsenosides.

In one aspect to achieve the above objects, the present invention provides a Rhodanobacter ginsenosidimutans KCTC22231T-derived ginsenoside glycosidase protein (hereinafter, interchangeable with 'protein of the present invention' or 'ginsenoside glycosidase').

As used herein, the term 'ginsenoside glycosidase' or 'ginsenoside glycosidase protein' is a kind of glycosidase which catalyzes the hydrolysis of glycosidic linkage of polysaccharide chains. Any enzyme can be used without limitation, as long as it has an activity of the biotransformation of ginsenoside. There are differences in the activity and function between the enzymes.

The protein of the present invention is an enzyme that is derived from Rhodanobacter ginsenosidimutans KCT22231T, and has an activity of converting PPD-type saponins into in vivo absorbable saponins. More preferably, the protein of the present invention has an activity of selectively hydrolyzing the saccharide at the C-20 or C-3 position of PPD-type saponin.

The saccharide preferably glucosylpyranoside or arabinopyranoside, but is not limited thereto.

A microorganism for identifying the novel nucleic acid of the present invention is Rhodanobacter ginsenosidimutans KCT22231T, and the present inventors isolated the KCT22231T strain from a ginseng farm in Po-chun, Korea.

The protein of the present invention has an amino acid sequence (polypeptide sequence) constituting Rhodanobacter ginsenosidimutans KCTC22231T-derived ginsenoside glycosidase. The amino acid sequence is preferably a sequence represented by SEQ ID NO. 2, and includes an amino acid sequence having 70% or higher homology, preferably 80% or higher homology, more preferably 90% or higher homology, much more preferably 95% or higher homology, and most preferably 98% or higher homology with the sequence, and includes proteins substantially having the ginsenoside glycosidase activity. Further, it is apparent that any type of protein variants having a deletion, modification, substitution or addition of some sequence may be within the scope of the present invention, as long as the sequence having the homology is an amino acid sequence having a biological activity that is substantially identical or corresponding to the ginsenoside glycosidase.

In another aspect, the present invention provides a nucleic acid encoding Rhodanobacter ginsenosidimutans KCTC22231T-derived ginsenoside glycosidase.

The nucleic acid of the present invention is a nucleic acid encoding Rhodanobacter ginsenosidimutans KCTC22231T-derived ginsenoside glycosidase, and the nucleic acid encoding ginsenoside glycosidase isolated from the strain is preferably a nucleic acid represented by SEQ ID NO. 1, and includes a sequence having 70% or higher homology, preferably 80% or higher homology, more preferably 90% or higher homology, much more preferably 95% or higher homology, and most preferably 98% or higher homology with the sequence, and includes nucleic acids that substantially encode proteins having the ginsenoside glycosidase activity.

According to one embodiment of the present invention, the nucleic acid of the present invention was designated as bgl3054 (hereinafter, interchangeable with 'BGL 3054') by the present inventors, and the nucleic acid includes a nucleic acid of 1302 bp in length, and encodes a polypeptide consisting of 433 amino acids.

As used herein, the term 'homology' is intended to indicate the degree of similarity to the amino acid sequence of a wild type protein or a base sequence encoding the same, and includes sequences having homology of the above percentage or higher with the amino acid sequence or base sequence of the present invention. Homology comparisons can be conducted by eye or with the aid of readily available sequence comparison programs. A commercially available computer program may express homology between two or more sequences as a percentage, and a homology (%) may be calculated for adjacent sequences.

Those skilled in the art will readily appreciate that artificially modified proteins are also equivalent to the protein as long as they maintain homology greater than a predetermined level and retain the activity of the desirable protein. Therefore, the protein of the present invention includes amino acid sequence variants and base sequence variants of a wild-type, and the term 'variant' means a protein or a nucleic acid in which one or more amino acid residues or base sequences differ from the native amino acid sequence or base sequence, resulting from a deletion, an insertion, a non-conservative or conservative substitution or combinations thereof.

In still another embodiment, the present invention provides a recombinant vector including the nucleic acid encoding Rhodanobacter ginsenosidimutans KCTC22231T-derived ginsenoside glycosidase.

Figure 9:
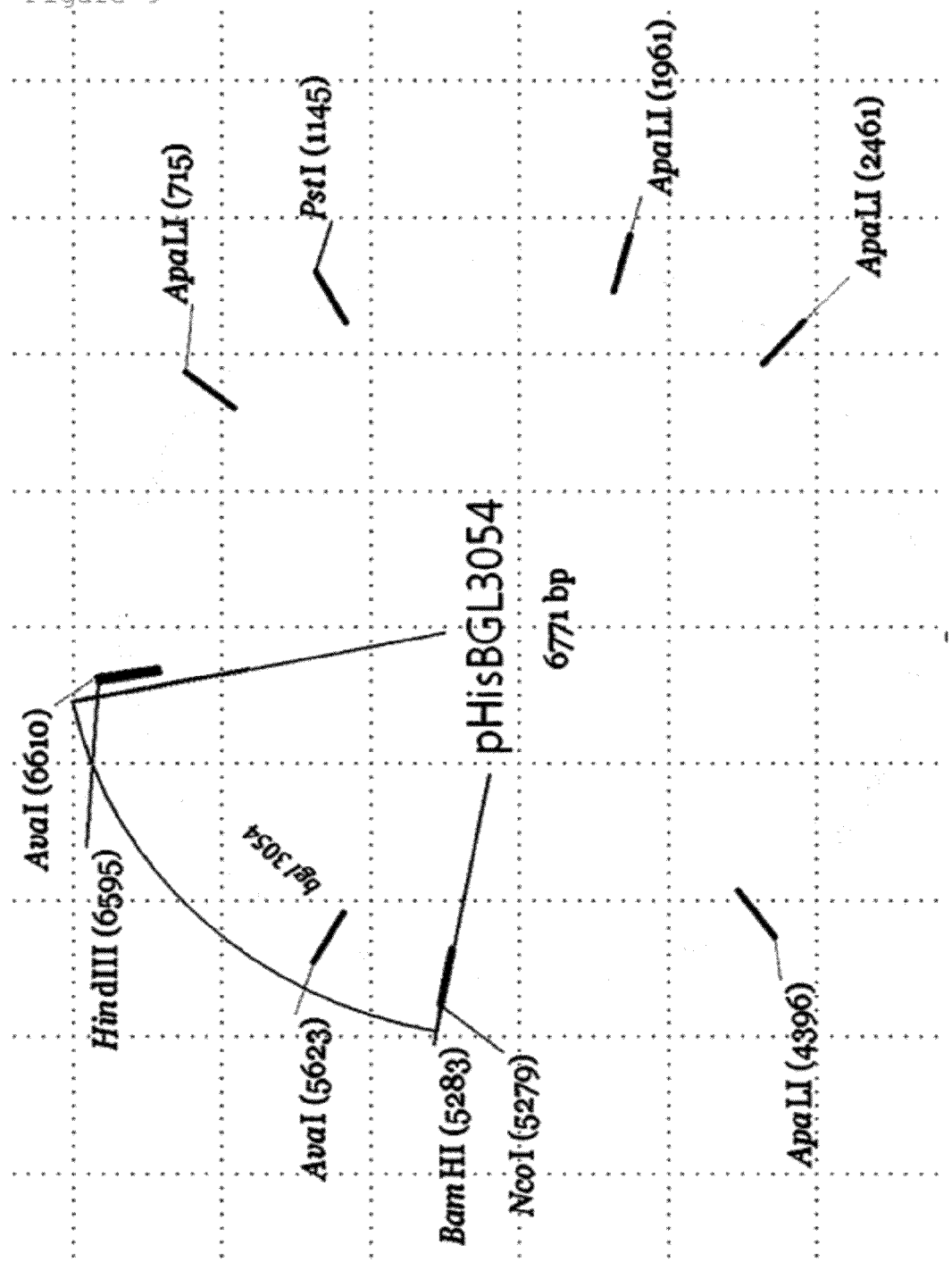
FIG. 9 illustrates a plasmid vector including Bgl 3054.

As used herein, the term 'vector' is an expression vector for expressing a desired protein in a proper host cell, and refers to a DNA construct including essential regulatory elements operably linked to express a nucleic acid insert. In the present invention, a recombinant vector including the nucleic acid encoding ginsenoside glycosidase can be constructed, and a host cell is transformed or transfected with the constructed recombinant vector, thereby obtaining the protein of the present invention. In the specific Example of the present invention, fosmid library screening was performed, and ORF encoding ginsenoside glycosidase was identified, and inserted into a pHis-Parallell expression vector, thereby preparing a recombinant vector pHisBGL3054 (FIG. 9).

The recombinant vector of the present invention can be obtained by linking (inserting) the nucleic acid of the present invention with a proper vector. The vector, into which the nucleic acid of the present invention is inserted, is not particularly limited, as long as it is replicable in the host cell. It is exemplified by plasmid DNA, phage DNA or the like. The specific example of plasmid DNA includes commercial plasmids such as pCDNA3.1+ (Invitrogen). Other examples of the plasmid used in the present invention include *E.coli*-derived plasmids (pYG601BR322, pBR325, pUC118 and pUC119), *Bacillus subtilis*-derived plasmids (pUB110 and pTP5), and yeast-derived plasmids (YEp13, YEp24 and YCp50).

The specific example of phage DNA includes λ-phages (Charon4A, Charon21A, EMBL3, EMBL4, λgt10, λgt11 and λZAP). Further, animal virus such as retrovirus, adenovirus or vaccinia virus, and insect virus such as baculovirus may be used. In the specific Example of the present invention, the recombinant vector pHisBGL3054 was prepared by insertion into the pHis-Parallel1 vector.

Moreover, as the vector of the present invention, a transcriptional activator (such as B42)-linked fusion plasmid (e.g., pJG4-5) may be used, and GST, GFP, His-tag, Myc-tag may be applied to the fusion plasmid, but the fusion plasmid of the present invention is not limited to these examples. In the specific Example of the present invention, in order to facilitate purification and recovery of the expressed ginsenoside glycosidase, a hexahistidine tag (6× his tag, His6 tag) was used.

For insertion of the nucleic acid of the present invention into the vector, the purified DNA may be cleaved using proper restriction enzymes, and inserted into the restriction sites or cloning site of a proper vector DNA. According to the specific Example of the present invention, Bgl 3054 gene was inserted between the restriction sites of BamHI and HindIII, as indicated by the arrows.

The nucleic acid of the present invention should be operably linked to a vector. The vector of the present invention may further include cis elements such as an enhancer, a splicing signal, a poly A addition signal, a selection marker, a ribosome binding sequence (SD sequence), in addition to a promoter and the nucleic acid of the present invention. The selection marker may be exemplified chloramphenicol resistance gene, ampicillin resistance gene, dihydrofolate reductase, neomycin resistance gene or the like, but the operably linked additional elements are not limited to these examples.

In still another embodiment, the present invention provides a transformant that is transformed with the vector including the nucleic acid encoding ginsenoside glycosidase.

As used herein, the term 'transformation' means introduction of DNA into a host cell so that DNA is replicable, either as an extra-chromosomal element or by chromosomal integration, that is, artificial genetic alteration by introducing a foreign DNA into a host cell.

The transformation of the present invention may be performed by any transformation method, and is easily performed according to a typical method known in the art. In general, examples of the transformation method include a CaCl2 precipitation, a Hanahan method that is an improved CaCl2 method by using DMSO (dimethyl sulfoxide) as a reducing material, electroporation, calcium phosphate precipitation, protoplast fusion, agitation using silicon carbide fiber, Agrobacterium-mediated transformation, PEG-mediated transformation, dextran sulfate-, lipofectamine-, and desiccation/inhibition-mediated transformation.

The transformation method for the vector including the nucleic acid encoding ginsenoside glycosidase of the present invention is not limited to these examples, and the transformation or transfection methods typically used in the art may be used without limitation.

The transformant of the present invention can be obtained by introducing the recombinant vector including the desired nucleic acid encoding ginsenoside glycosidase into a host cell.

The host cell is not particularly limited, as long as it is able to express the nucleic acid of the present invention. The specific examples of the host cell to be used in the present invention include bacteria belonging to the genus *Escherichia* such as *E. coli*; bacteria belonging to the genus *Bacillus* such as *Bacillus subtilis*; bacteria belonging to the genus *Pseudomonas* such as *Pseudomonas putida*; yeasts such as *Saccharomyces cerevisiae* and *Schizosaccharomyces pombe*; animal cells, and insect cells.

The specific example of the *E. coli* strain to be used in the present invention include CL41(DE3), BL21, and HB101, and the specific examples of the *Bacillus subtilis* strain include WB700 and LKS87. In the specific Example of the present invention, *E.coli* CL41(DE3) was used as a host cell to prepare the transformant that is transformed with the vector including ginsenoside glycosidase.

When bacteria such as *E.coli* are used as host cells, the recombinant vector of the present invention is able to autonomically replicate in the host cells, and consists of a promoter, a ribosome binding sequence, the nucleic acid of the present invention, and a transcription termination sequence.

Any promoter can be used as the promoter of the present invention, as long as it is able to drive expression of the nucleic acid of the present invention in the host cell such as *E.coli*. For example, *E.coli* or phage-derived promoters such as trp promoter, lac promoter, PL promoter, and PR promoter, and *E.coli* infection phage-derived promoters such as T7 promoter may be used. In addition, artificially modified promoters such as tac promoter may be used.

In order to facilitate purification of the desired protein recovered in the present invention, the plasmid vector may further include other sequences, if necessary. The sequences further included may be tag sequences for protein purification, for example, glutathione S-transferase (Pharmacia, USA), maltose binding protein (NEB, USA), FLAG (IBI, USA), and hexahistidine (Quiagen, USA), and most preferably hexahistidine. However, the type of the sequences needed for the purification of the desired protein is not limited to these examples. In the specific Example of the present invention, a hexahistidine tag was used to facilitate the purification.

Further, the fusion protein expressed by the vector including the fusion sequence may be purified by affinity chromatography. For example, if glutathione S-transferase is fused, its substrate glutathione can be used. If hexahistidine is used, a Ni-NTA His-bind resin column (Novagen, USA) can be used to facilitate the recovery of the desired protein.

In still another embodiment, the present invention provides a method for preparing Rhodanobacter ginsenosidimutans KCTCC22231T-derived ginsenoside glycosidase. Preferably, the preparation method may include the steps of (a) culturing the transformant that is transformed with the vector including the nucleic acid encoding ginsenoside glycosidase; (b) producing ginsenoside glycosidase from the cultured transformant; and (c) recovering the produced ginsenoside glycosidase.

The method of expressing ginsenoside glycosidase of the present invention is the same as described above, and the host cell transformed by the above method can be cultured by typical method used in the art. For example, the transformant expressing ginsenoside glycosidase may be cultured in various media, and fed-batch culture and continuous culture may be performed, but the method of culturing the transformant of the present invention is not limited to these examples. In addition, a carbon source included in the media for growing the host cell may be properly selected by those skilled in the art depending on the type of the prepared transformant, and suitable culture conditions may be adopted to adjust the culture time and amount.

When a proper host cell is selected and cultured under the culture conditions, the transformant that is successfully transformed with the desired protein produces ginsenoside glycosidase, and ginsenoside glycosidase produced according to the vector construction and properties of the host cell can be released into the cytoplasm, periplasmic space, or out of the cells. In addition, the desired protein may be expressed in a soluble or insoluble form.

The protein expressed inside or outside the host cell may be purified in a typical manner. The purification method is exemplified by salting out (e.g., ammonium sulfate precipitation, sodium phosphate precipitation), solvent precipitation (e.g., protein fractional precipitation using acetone or ethanol) , dialysis, gel filtration, ion exchange, chromatography such as reversed phase column chromatography, and ultrafiltration, and these methods may be performed singly or in combination to purify the protein of the present invention.

Absorbable saponin can be produced using the ginsenoside glycosidase isolated by the above method in an in-vitro or in vivo system containing ginsenoside.

In still another embodiment, the present invention provides a method for converting PPD-type saponins into in vivo absorbable saponins using the Rhodanobacter ginsenosidimutans KCTC22231T-derived ginsenoside glycosidase.

As the PPD-type saponin used as a starting material in the present invention, isolated and purified saponin, or saponin included in the powder or extract of ginseng or red ginseng may be used. That is, the powder or extract of ginseng or red ginseng including saponin may be directly used as a starting material to perform the method of the present invention. The ginseng used in the present invention includes the known various ginsengs, such as *Panax ginseng, Panax quiquefolius (P. quiquefolius), Panax notoginseng (P. notoginseng), Panax japonicus (P. japonicus), Panax trifolium (P. trifolium), Panax pseudoginseng (P. pseudoginseng)* and *Panax vietnamensis (P. vietnamensis)*, but is not limited thereto.

As mentioned in ginsenosides are classified into three groups based on their aglycone structure: Protopanaxadiol-type ginsenosides, Protopanaxatriol-type ginsenosides, and Oleanolic acid-type ginsenosides. The PPD-type saponin of the present invention means Protopanaxadiol-type ginsenosides.

The Rhodanobacter ginsenosidimutans KCTC22231T-derived ginsenoside glycosidase of the present invention is used to convert it into the in vivo absorbable saponin, which means that the unabsorbable major PPD-type saponins (e.g., ginsenoside Rb1, Pb2, Rc) can be converted into the in vivo absorbable minor saponins (e.g., ginsenoside F2, Mc1) by selective hydrolysis of a glycosidic bond at the specific position and subsequent hydrolysis of a saccharide at C-20 or C-3 position of the PPD-type saponins.

Preferably, the conversion may occur through bioconversion, and it may be achieved by continuous or discontinuous selective hydrolysis of a saccharide at the C-20 or C-3 position of the PPD-type saponins.

The saccharide is preferably glucosylpyranoside or arabionopyranoside, but is not limited thereto.

The protein of the present invention is able to convert all of the PPD-type saponins known in the art into the absorbable minor saponins, and the preferred examples of the bioconversion by the protein of the present invention include conversion of ginsenoside Pb1 into Rd, conversion of the converted Rd into F2, conversion of ginsenoside Rb2 into Rd, conversion of the converted Rd into F2, and conversion of ginsenoside Rc into compound Mc1.

More particularly, in the specific Example of the present invention, Rd and F2 were sequentially produced by addition of the composition including the protein of the present invention to ginsenoside Rb1 and Rb2. In addition, it was found that compound Mc1 was produced by addition of the protein of the present invention using ginsenoside Rc as a starting material. These procedures may be performed by hydrolysis of a saccharide at the C-20 or C-3 position of the PPD-type saponins using the protein of the present invention, and the products (ginsenoside derivatives) produced by the hydrolysis are more absorbable than the reacting materials.

The protein of the present invention is an enzyme for converting PPD-type saponins into absorbable saponins, and can be used under various temperature and pH conditions as long as its activity and stability are maintained. It may be used together with one or more metals or chemical agents selected from the group consisting of $ZnCl_2$, $MnCl_2$, $CaCl_2$, $CoCl_2$, $MgCl_2$, EDTA, NaCl, KCl, $CuCl_2$, SDS, DTT, and mercaptoethanol, but is not limited thereto.

Figure 6:
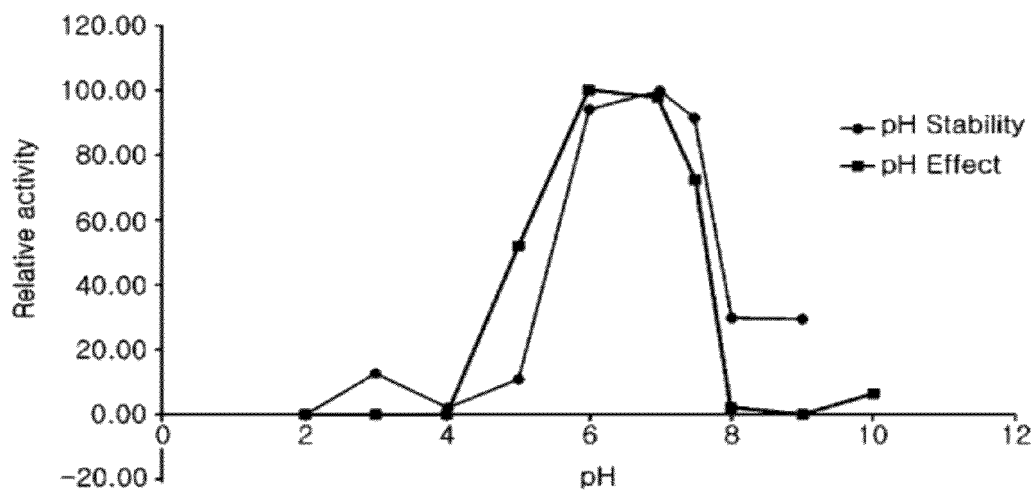
FIG. 6 is a graph showing stability and activity of Bgl3054 purified from *E.coli* according to pH.
Figure 7:
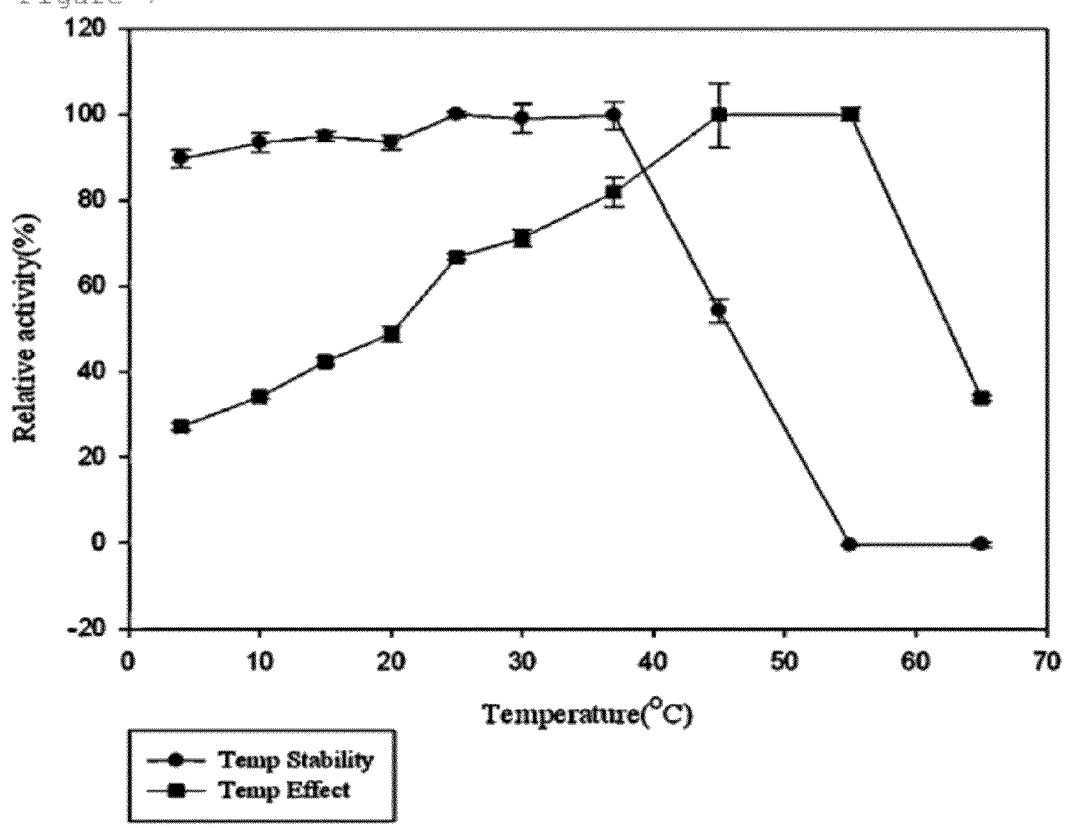
FIG. 7 is a graph showing stability and activity of Bgl3054 purified from *E.coli* according to temperature.

According to the specific Example of the present invention, characterization of the enzyme of the present invention showed that it had excellent stability at 37° C. or lower, high stability at 40-55° C., and it had excellent stability and activity at pH 5.5-7.5 (FIGS. 6 and 7).

In still another embodiment, the present invention provides a composition for converting PPD-type saponins into in vivo absorbable saponins, including Rhodanobacter ginsenosidimutans KCTC22231T-derived ginsenoside glycosidase as an active ingredient.

Hereinafter, the present invention will be described in more detail with reference to Examples. However, these Examples are for illustrative purposes only, and the invention is not intended to be limited.

Mode for Invention

Example 1

Fosmid Library Screening and Full Sequence Analysis

A CopyControl Fosmid Library Production Kit (Epicentre, U.S.A) was used according to the manufacturer's instructions. The genomic DNA of Rhodanobacter ginsenosidimutans KCTC22231T was randomly cleaved to a fragment of approximately 40 Kb. A small amount thereof was electrophoresed by Pulsed Field Gel Electrophoresis to determine the size of the cleaved DNA. The blunt, 5'-phosphorylated end was prepared by end-repair. The end-repaired DNA of 40 Kb or longer was selected by LMP (low melting point) agarose gel electrophoresis. The blunt end DNA was purified from the LMP agarose gel, and ligated into a pCC1FOS vector. A MaxPlax lambda packaging extract kit (Epicentre, U.S.A.) was used to perform in vitro packaging. Finally, the product was transfected *E.coli* EPI300-T1R that was cultured in LB broth containing 10 mM $MgSO_4$ until the OD value at 600 nm reached 0.6. Absorption of the transfected bacteria was allowed at 37° C. for 20 minutes, and the bacteria were spread on a LB plate containing 12.5 μg/ml chloramphenicol and 27β-X-gal (5-Bromo-4-chloro-3-indolyl-beta-D-glucoside) and cultured at 37° C. After 16-20 hours, blue colonies (putative ginsenoside glycosidase-producing clones) were selected, and the activity was further examined on the same plate. Then, the putative clones were cultured in 0.2 ml of LB broth containing 12.5 μg/ml chloramphenicol at 37° C. for 24 hours.

For analysis of ginsenoside-hydrolytic ability, TLC analysis was used. The fosmid DNA converting ginsenoside Rb1 into Rd, putative as a pbgl3054-p1 fosmid clone, was identified from the cell culture, and purified using a FosmidMAX DNA purification kit (Epicentre, U.S.A) according to the manufacturer's instructions. The purified fosmid DNA was analyzed by full sequencing. Transposon insertion was performed using a HyperMuTm<KAN-1> Insertion Kit (Epicentre, U.S.A) according to the manufacturer's protocol. Sequencing of selective insertion clones was performed using two primers of MUKAN-1 FP-1 [5'-CTGGTCCACCTA-CAACAAAGG-3' (SEQ ID NO. 3)] and MUKAN-1 RP-1 [5'-AGAGATTTTGAGACAGGATCCG-3' (SEQ ID NO. 4)] in both directions, thereby obtaining a full sequence, which contains the terminal similarity region of HyperMu transposon inserted in the kit. An ABI PRISM™, Bigdye™, Cycle Sequencing Ready Reaction Kit (Applied Biosystems, Foster City, Calif.) was used as a template to perform DNA base sequence determination reaction. Data collection and analysis were performed using an ABI 3730XL caillary DNA Sequencer (Applied Biosystems, Foster City, Calif.).

Example 2

Molecular Cloning, Expression, and Purification of bgl3054

(2-1) Molecular Cloning and Expression of bgl3054

The assembled DNA sequence of pbgl3054-p1 was analyzed using a genetic code 1 and Vector NTI v10.0 (Invitrogen Inc.). ORF of ginsenoside glycosidase was found, and the template pbgl3054-p1 DNA was amplified by PCR using the following oligonucleotide primers.

```
Forward primer:
                                    (SEQ ID NO. 5)
5'-CGG ATC CAA TGG GCC TGG GAC GCC GGC GT-3'

Reverse primer:
                                    (SEQ ID NO. 6)
5'-CGG AAG CTT TCA GGC GGG CTG CGG TGC-3'
```

The amplified fragment was sequentially cloned into a pHis-Parale1 expression vector (used by introduction of EcoRI and HindIII restriction sites) and a recombinant TEV protease (rTEV)-containing His6 (hexahistidine) fusion protein expression vector, pHis-Parallel1. Next, the recombinant vector pHisBGL3054 was introduced into *E.coli* C41 (DE3).

(2-2) The Results of Cloning and Expression of bgl3054

The ginsenoside glycosidase showed the ability of converting ginsenoside Rb1 into Rd, and thus the present inventors designed the ORF with bgl3054. The putative amino acid sequence of bgl3054 had 433 residues and a molecular weight of 49 kDa.

(2-3) Purification of bgl3054

*E.coli* C41 (DE3) containing overexpressed plasmid was cultured in LB-ampicillin media at 37° C. when the OD value at 600 nm reached 0.6, and treated with 0.5 mM isopropyl-β-D-thiogalactopyranoside for 12 hours to induce protein expression. The bacterial cells were obtained by centrifugation at 4° C. and 5,000×g for 20 minutes. The cell pellet was resuspended in a solution (suspension) consisting of 50 mM sodium phosphate, 5 mM EDTA, and 1% Triton X-100 (pH 7.0) and subjected to ultrasonification. Ginsenoside glycosidase was completely hydrated without formation of insoluble precipitate, and ginsenoside glycosidase was reacted with 1 mg/ml Rb1 solution in 50 mM sodium phosphate, and TLC analysis was performed.

As a result, ginsenoside glycosidase Bgl3054 converted ginsenoside Rb1 into F2 via Rd. The ginsenoside glycosidase Bgl3054-encoding nucleic acid was designed with bgl3054. Therefore, bgl3054 was loaded on a Nickel-charged HisTrap column (HisTrap HP, 5 ml bed volume, Gel health), and pre-equilibrated with buffer A (50 mM sodium phosphate, pH 7.0) at 4° C. The resin was washed with buffer A, and the binding protein was eluted with buffer A containing 200 mM imidazole. His6-tag was separated from the protein by culturing rTEV according to the HisTrap column, and additional purification was performed on the column containing 30 ml DEAE-cellulose DE-52 (Whatman) using 50 mM sodium phosphate at pH 7.0 and 300 mM NaCl. Protein similarity was determined by 10% SDS-PAGE and Coomassie Blue staining. Dialysis of the purified protein was performed at a concentration of 10 mg/ml using an Amicon Ultra-15 filter (Millipore, U.S.A) and 50 mM sodium phosphate at pH 7.0, and stored at −80° C. until use.

Enzyme analysis and kinetic analysis were performed using the His6-tagged protein purified using 50 mM sodium phosphate at pH 7.0. Gel-filtration analysis was performed on a Sepharose 6 10/300GL (GE Healthcare) column.

Measurement was performed using Bio-Rad filtration standard (catalog no. 151-1901). The resulting enzyme purification scheme was shown in Table 1.

(2-4) Result of bgl3054 Purification

Figure 3:
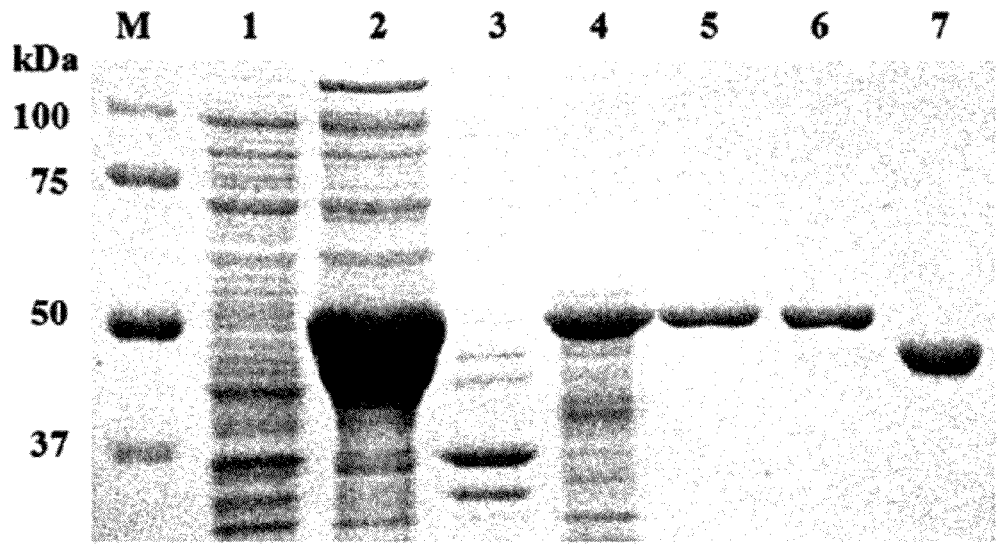
FIG. 3 shows the results of SDS-PAGE for purification of bgl3054 (M, molecular weight marker; lane 1, Crude cell before induction; lane 2, Cell-free extract after expression induction; lane 3, Precipitate after cell lysis; lane 4, Protein purified by Nickel-charged His Trap column; lane 5, Protein purified by DEAE anion-exchange column; lane 6, Protein purified by DEAE anion-exchange column; lane 7, His6 tag-removed protein by rTEV)
Figure 4:
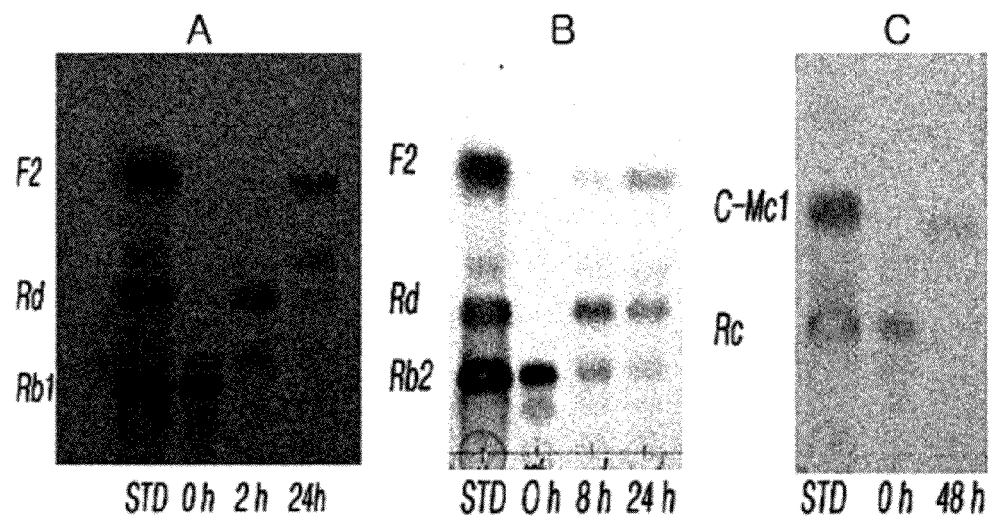
FIG. 4 is TLC photographs showing bioconversion activity of bgl3054 protein.

Gel filtration on Superose 6 10/300 GL (GE Healthcare) and SDS-PAGE showed that the natural ginsenoside glycosidase had a molecular weight of 49 kDa and 50 kDa, respectively. These results indicate that ginsenoside glycosidase is a monomeric protein (FIG. 3).

Example 3

Enzyme Characterization

Specific activity was measured using 90 μl of 50 mM sodium phosphate buffer containing 2.0 mM pNPGlc (p-nitrophenyl-β-D-glucopyranoside; Sigma) at pH 7.0, and 10 μl of the diluted purified enzyme was treated at 37° C. for 20 minutes before initiation of the reaction, followed by incubation. 0.1 ml of 1 M $Na_2CO_3$ was treated for 5 minutes to terminate the reaction, and the concentration of p-nitrophenol was immediately measured at 405 nm. One unit of activity was defined as the amount of enzyme that released 1 μmol of p-nitrophenol per minute. Specific activity is expressed in units per milligram protein. Protein concentration was measured using a Bio-Rad protein staining reagent according to the protocol. All analyses were performed at least three times.

(3-1) Measurement of pH Effects

The effect of pH on the enzymatic activity was measured. 2.0 mM pNPGlc (p-nitrophenyl-β-D-glucopyranoside; Sigma) was used as a substrate, and pH was adjusted using the following buffer (50 mM).

pH range of 2 to 10: KCl-HCl (pH 2), glycine-HCl (pH 3), sodium acetic acid (pH 4 and 5), sodium phosphate (pH 6 and 7), Tris-HCl (pH 8 and 9) and glycine-sodium hydroxide (pH 10) Further, the effect of pH on the enzymatic stability was measured. The enzyme was incubated in each of the above mentioned buffers at 4° C. for 24 hours, and then pHPGlc was analyzed in 50 mM potassium buffer to measure the enzymatic stability according to pH change. Residue activity was analyzed according to a standard analytical procedure, and the results are shown in FIG. 6 as an activity probability obtained at the optimum pH.

With reference to FIG. 6, bgl3054 showed excellent enzymatic stability and activity at pH 5.5-7.5 and the highest activity at pH 7.0 (FIG. 6).

(3-2) Measurement of Temperature Effects

The effect of temperature on the enzymatic activity was measured. The temperature was adjusted between 4-90° C., and 2.0 mM pNPGlc (p-nitrophenyl-β-D-glucopyranoside; Sigma) was used to analyze the temperature-dependent activity in the 50 mM potassium phosphate buffer at the optimum pH for 5 minutes.

Further, the equivalent amount of enzyme was incubated in 50 mM potassium phosphate buffer within the same temperature range for 30 minutes to analyze the temperature stability. The sample was cooled in ice for 10 minutes, and the residual activity was measured according to a standard analytical procedure, and the results are shown in FIG. 7.

As a result, the maximum activity of Bgl3054 was observed at 40-55° C., whereas thermal stability test showed that it was stable at 37° C. or lower, and 50% activity loss was observed at 45° C. after 30 minutes. Consequently, the maximum activity of Bgl3054 was observed at 40-55° C., whereas thermal stability was excellent at 37° C. or lower, in particular, almost half of the stability was lost at 45° C. (FIG. 7).

(3-3) Measurement of Metal and Chemical Agent Effects

Ginsenoside glycosidase was incubated at room temperature for 30 minutes in 1 mM and 10 mM (final concentration) of $ZnCl_2$, $MnCl_2$, $CaCl_2$, $CoCl_2$, $MgCl_2$, EDTA, NaCl, KCl, $CuCl_2$, DTT, SDS, and mercaptoethanol, and pNPGlc (p-nitrophenyl-β-D-glucopyranoside; Sigma) was used as a substrate to measure the activity. The resulting value was represented as a percentage to the obtained activity upon lack of the compounds, and is shown in Table 1.

It was found that most of the metal ions and chelating agents had minimal affect on the enzymatic activity, and SDS showed an inhibitory effect at the concentration of 10 mM or more.

(3-4) Measurement of Substrate Effects

A free PNP-type substrate has a yellow color, but turns colorless when it binds with various sugars. The characteristics of glucosidase-type enzymes were analyzed using this principle. For example, PNPGlc is a colorless compound prepared by beta linkage of PNP and glucose, but free PNP catalyzed by beta-glucosidase has a yellow color. Thus, when a color change occurs by use of PNPGlc as a substrate, the enzyme is determined as a beta-glucosidase. In addition, when PNP-β-D-galactopyranoside is metabolized by an enzyme to produce yellow color, it is determined as β-D-galactopyranosidase. The color becomes darker according to characteristics and concentrations of the substrate, and thus it is possible to measure the concentration of the enzyme using a spectrometer.

Therefore, substrate preference was analyzed by the following method in order to analyze the activity of Bgl305 of the present invention.

1 activity unit was defined as the release of o-nitrophenol or p-nitrophenol per minute. For analysis of substrate preference, 2.0 mM chromogenic ONP and PNP (p-nitrophenyl) were used as the substrates, and incubated in 50 mM sodium phosphate buffer at 37° C. for 5 minutes.

The analyzed substrates (Sigma) were PNP-β-D-glucopyranoside, PNP-β-D-galactopyranoside, PNP-β-D-fucopyranoside, PNP-N-acetyl-β-D-glucosaminide, PNP-β-L-arabinopyranoside, PNP-β-D-mannopyronoside, PNP-β-D-xylopyranoside, PNP-β-D-glucopyranoside, PNP-β-L-arabinofuranoside, PNP-β-L-arabinopyranoside, PNP-β-D-rhamnopyranoside, PNP-β-D-mannopyranoside, and PNP-β-D-xylopyranoside, and o-nitrophenol[ONP]-β-D-glucopyranoside, ONP-β-D-galactopyranoside, ONP-β-D-fucopyranoside, and ONP-β-D-galactopyranoside.

As a result, Bgl3054 showed the highest activity for ONP-β-D-fucopyranoside, and showed higher activity in this order of PNP-β-D-fucopyranoside, oNP-β-D-glucopyranoside, ONP-β-D-galactopyranoside, PNP-β-D-glucopyranoside, PNP-β-L-arabinopyranoside, and PNP-β-D-galactopyranoside.

This means that Bgl3054 has β-D-fucopyranosidase, β-D-glucopyranosidase, and β-L-arabinopyranosidase activities as well as β-D-glucosidase activity. In particular, the conversion of ginsenoside Rb2 into ginsenoside Rd is attributed to β-L-arabinopyranosidase activity of the present enzyme. That is, the enzyme is able to break the β-L-arabinopyranosidic bond at the C-20 position of ginsenoside Rb2, leading to the production of ginsenoside Rd (Table 3).

Further, kinetic studies were performed with freshly purified enzyme using pNPGlc (p-nitrophenyl-β-D-glucopyranoside; Sigma) at the concentrations of from 0.1 mM to 0.6 mM. Its absorbance at 405 nm was monitored at 37° C. for 20 minutes. The resulting data were used to determine Km and Vmax using the Enzyme Kinetics Program reported by Cleland.

Figure 8:
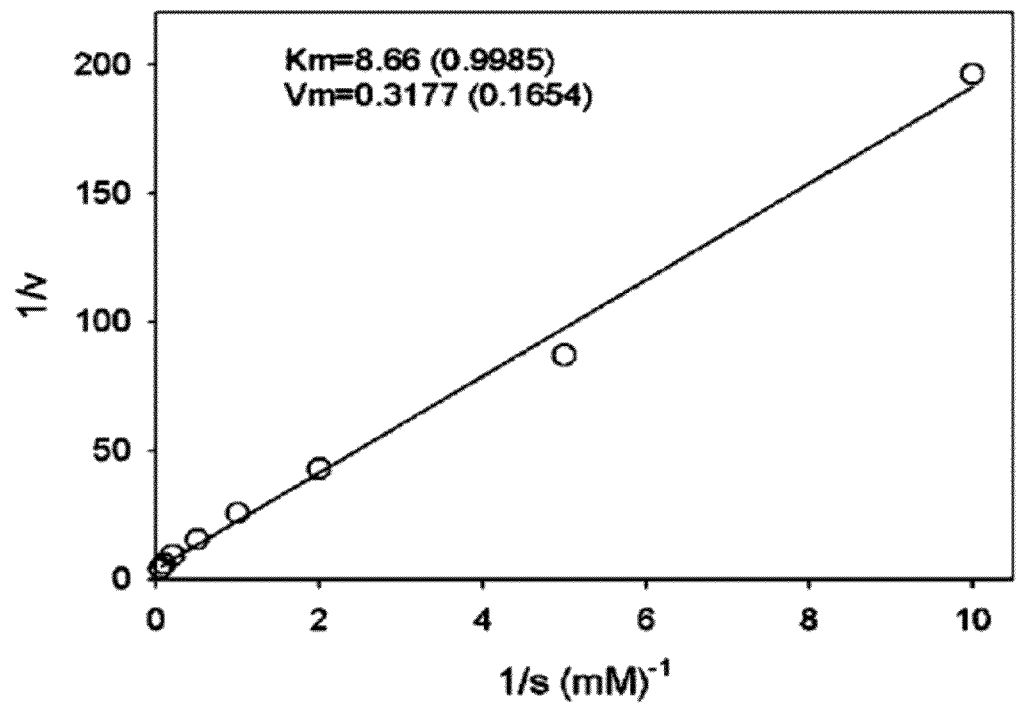
FIG. 8 is a double reciprocal graph showing Km and Vmax of the Bgl3054 protein according to the present invention.

Km and Vmax for the hydrolysis of pNPGlc (p-nitrophenyl-β-D-glucopyranoside; Sigma) by ginsenoside glycosidase were calculated using the Enzyme Kinetics Program reported by Cleland. Km and Vmax for pNPGlc (p-nitrophenyl-β-D-glucopyranoside; Sigma) were 8.66(±0.99885) mM and 0.3177(±0.01654) mmol*min−1*mg of protein-1, respectively (FIG. 8).

Example 4

Analysis on Specificity and Selectivity of the Enzyme

Figure 10:
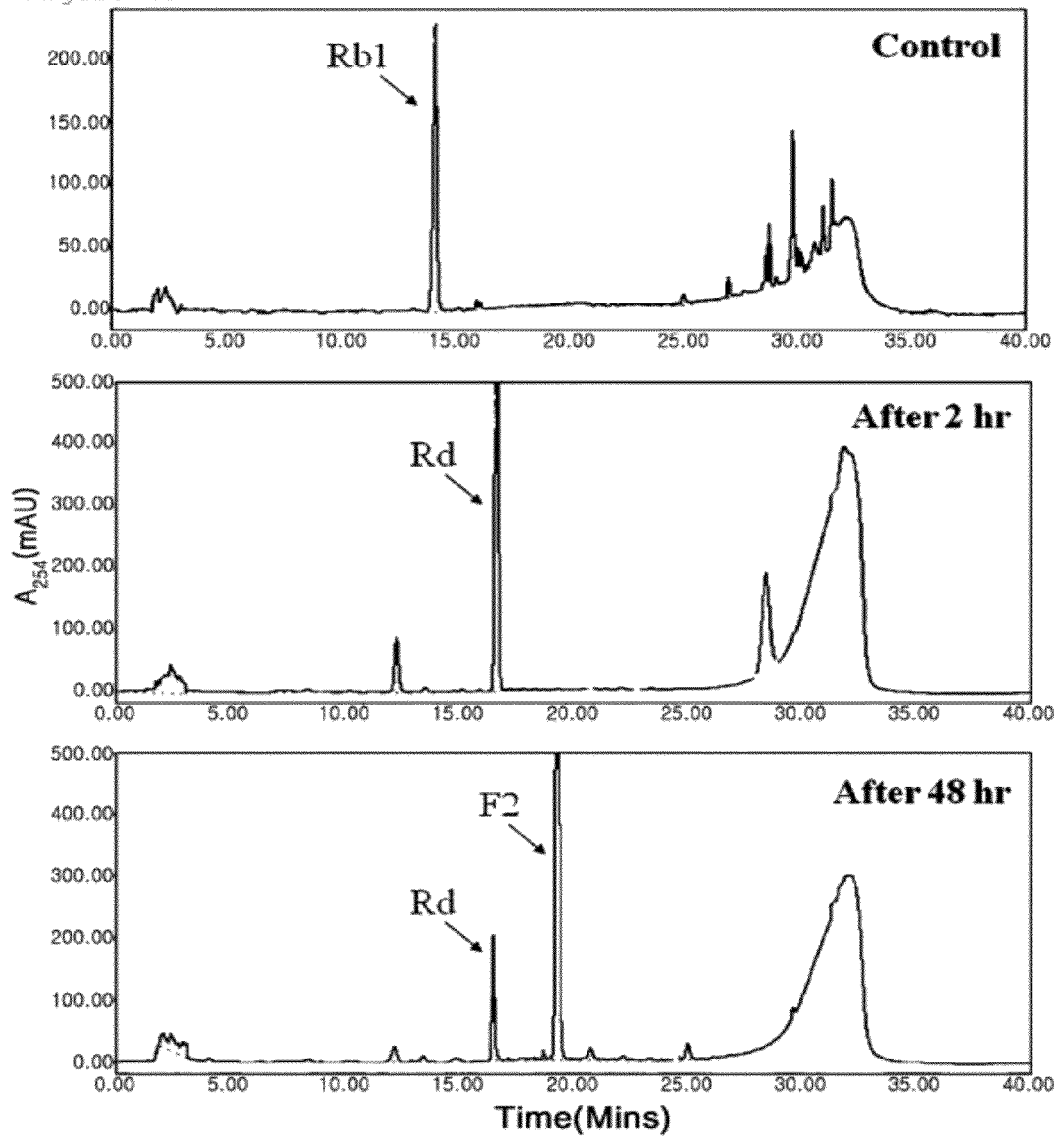
FIG. 10 is the result of HPLC showing time course of the bioconversion of Rb1_Rd_F2 using Bgl 3054.
Figure 11:
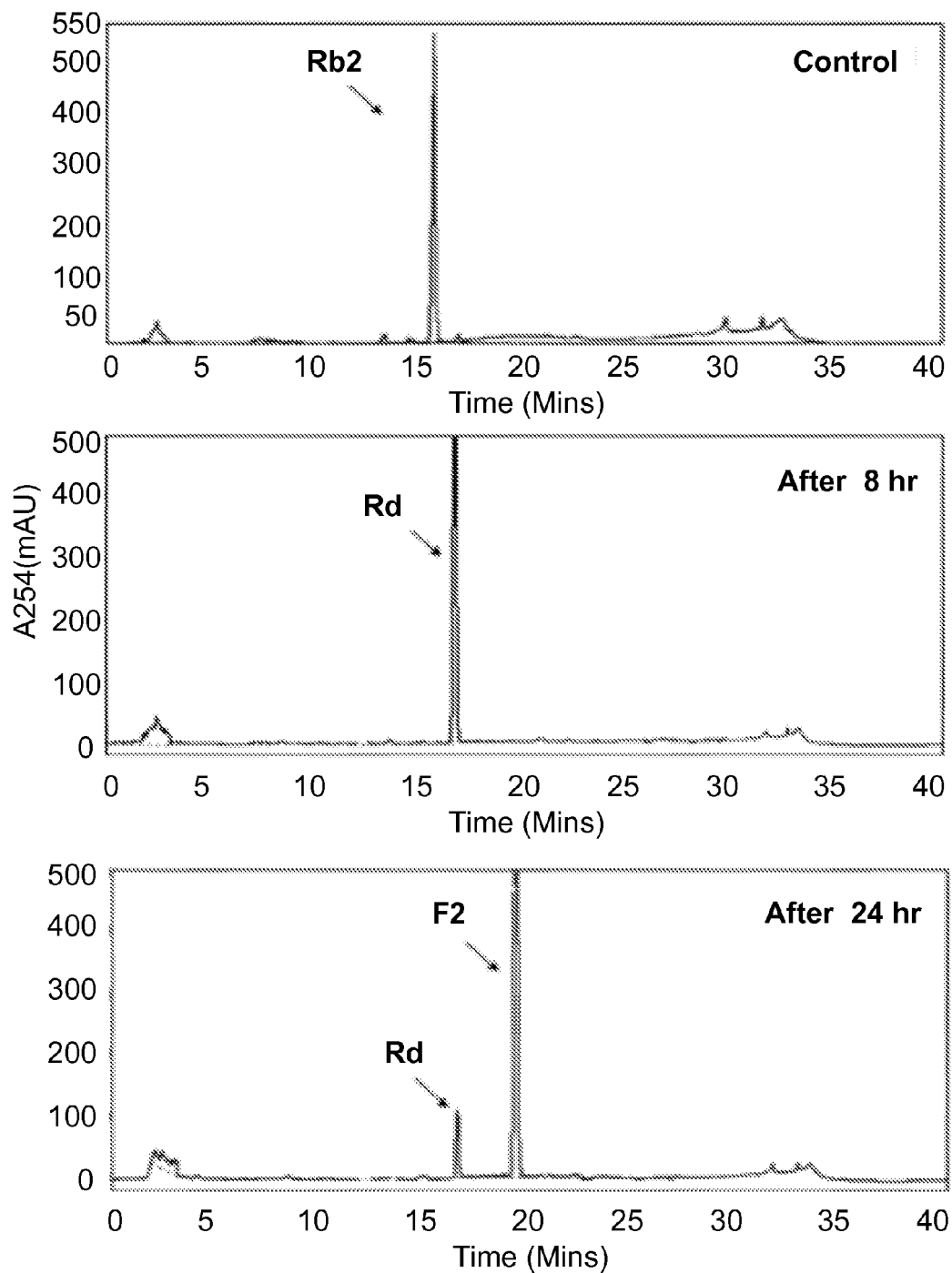
FIG. 11 is the result of HPLC showing time course of the bioconversion of Rb2_Rd_F2 using Bgl 3054.

In order to analyze the specificity and selectivity of the enzyme for the hydrolysis of glucose at the C-3 and C-20 positions of ginsenoside, ginsenoside Rb1, Rb2, Rc, Rd, and Rg3 were used as the substrates. Each reaction mixture containing 0.2U enzyme, 50 mM sodium phosphate buffer 0.1% (w/v) (pH 7.0), and the substrate was incubated at 37° C. Each sample was withdrawn at regular intervals, and an equal volume of water-saturated butanol was added to stop the reaction. The n-butanol fraction was evaporated to dryness, and residual material was dissolved in CH3OH and then examined by TLC HPLC or NMR analysis, and the results are shown in FIGS. 10, 11 and 12.

Figure 5:
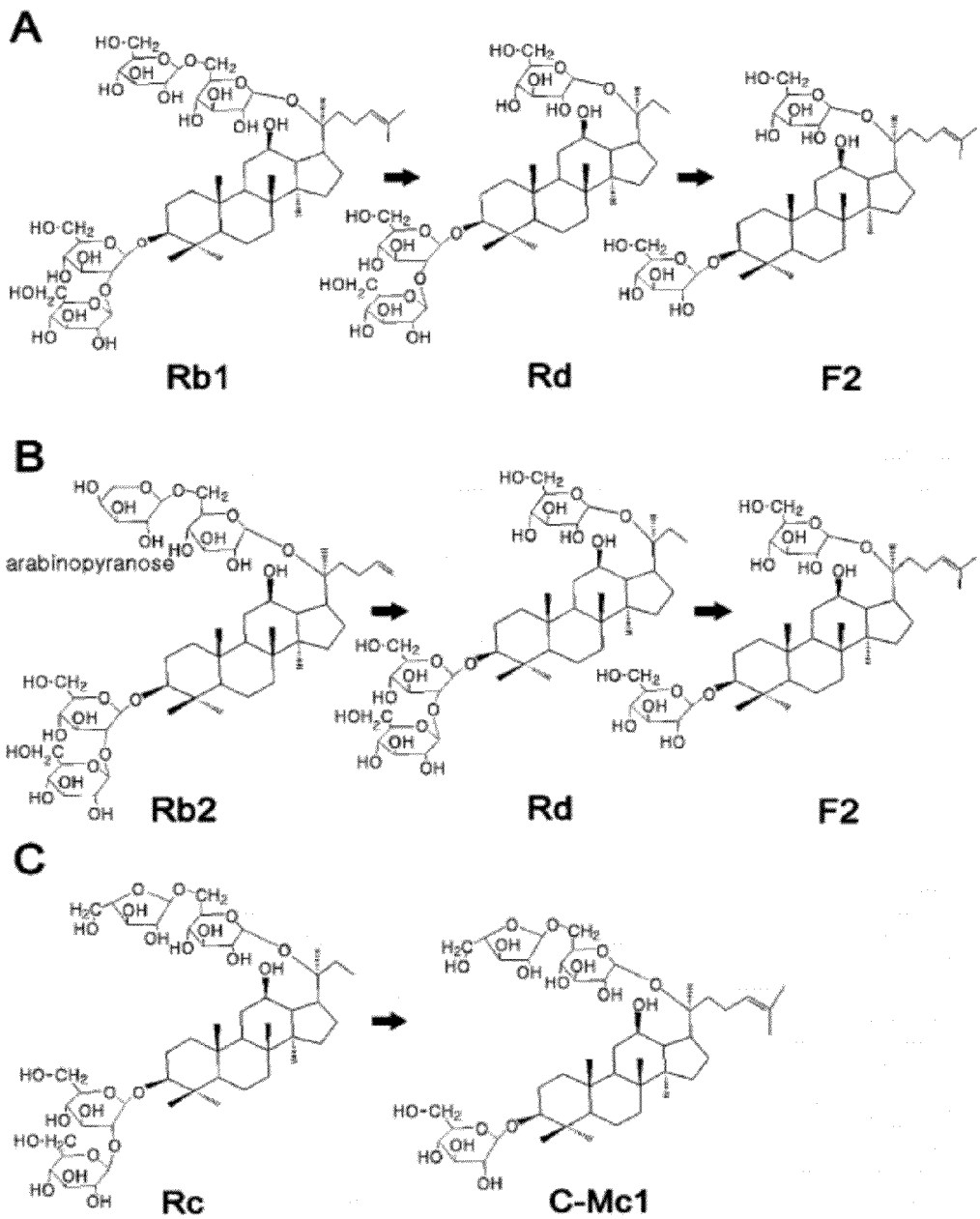
FIG. 5 is a schematic diagram showing bioconversion pathway of bgl3054 protein.

Ginsenoside Rb1 and Rb2 were converted into Rd by cleavage of the terminal glucose and arabinopyranoside at the C-20 position of Rb1, and then Rd was converted into F2 by cleavage of the terminal glucose at the C-3 position. Ginsenoside Rc was converted into compound Mc1 by cleavage of the terminal glucose at the C-3 position (FIG. 5).

The invention claimed is:

1. A recombinant vector comprising a nucleotide sequence that encodes a polypeptide having an amino acid sequence shown in SEQ ID NO. 2 and is operably linked to regulatory elements that direct the production of said polypeptide in an expression host.

2. A transformant that is transformed with the recombinant vector of claim 1.

3. The transformant according to claim 2, wherein the transformant is E. coli.

4. A method for preparing a polypeptide having an amino acid sequence shown in SEQ ID NO: 2, comprising the steps of:
   (a) culturing the transformant of claim 2; and
   (b) producing and recovering the polypeptide from the cultured transformant, wherein the polypeptide has an activity of converting PPD (protopanaxadiol)-type saponins into in vivo absorbable saponins.

5. A method for converting PPD (protopanaxadiol)-type saponins into in vivo absorbable rare saponins using the recombinant vector of claim 1, comprising the steps of:
   (a) transforming a host cell with the recombinant vector of claim 1 to obtain a transformant,
   (b) culturing the transformant under conditions that induce expression of the polypeptide of SEQ ID NO: 2;
   (c) producing and recovering the polypeptide from the cultured transformant,
   (d) treating PPD-type saponins with the polypeptide, thereby converting it into absorbable rare saponins.

6. The method according to claim 5, wherein the method is performed by hydrolysis of a saccharide at the C-20 or C-3 position of PPD-type saponin.

7. The method according to claim 6, wherein the saccharide is glucosylpyranoside or arabionopyranoside.

8. The method according to claim 5, wherein the conversion is one or more selected from the group consisting of conversion of ginsenoside Rb1 or ginsenoside Rb2 into ginsenoside Rd, conversion of ginsenoside Rd into ginsenoside F2, and conversion of ginsenoside Rc into compound Mc1.

9. The method according to claim 5, wherein the conversion is performed at pH 5.5 to 7.5 and a temperature of 30 to 55° C.

* * * * *

SEQUENCE LISTING

```
<160> NUMBER OF SEQ ID NOS: 6

<210> SEQ ID NO 1
<211> LENGTH: 1302
<212> TYPE: DNA
<213> ORGANISM: Artificial Sequence
<220> FEATURE:
<223> OTHER INFORMATION: Bgl3054

<400> SEQUENCE: 1
ggcctgggac gccggcgtgc gtccatgatg agaggaaccc caatgaccaa cccgtttccg      60
caggacttcc tttggggcgt ggccaccgca ggccaccagg tggaaggcaa caacgtcaac     120
agcgatgtct ggttcctgga acaccttccg ggcaccattt tcgcggagcc gtccggggat     180
gccgtggacc actaccaccg gtaccgggag gatattgccc tgatcgccgg cctcggtttt     240
accagctacc ggttctccgt ggaatgggcc cggatcgaac cggaggaagg gcatttctcg     300
gtggctgcgc tggaccacta caagcgggtg ctcgaggcct gccgggagca cgggctgacg     360
ccggtggtca cgttccacca tttcgcgtca ccgctgtggc tgctccgttc gggcggctgg     420
gagggcgaac gcacgccgga gctgttcgcc cgctattgcg gccgggtcat ggcgcacctg     480
ggtgacctga tcggcgtcgc ctgcaccctg aacgagccca acctcccttg gctgctggag     540
```

```
tcattcggca tcggcgggga agcgccgag  aaccgcggca aggtccccat gtgggcggct    600
gccgcacagc gcctgggcgt ggacgccagc acgttgccc  cgttccagtt ctgctccacg    660
gaggccggct tcaacgttaa actcgcggcg cacaaggcgg ccaccgaagc aatcaaggca    720
caccgcccgg atctgcgcgt gggctggacc ttggccaact cggacatcca gtcggtcccc    780
ggcggcgaag aaatcgcggc ccaggtgcgc cgggacgtca acgagcggtt cctggaagcc    840
tcccgcggcg acgacttcgt gggcatccag acttacggcc gcaccgtgta cggcccggac    900
ggccacgctc cggctccgga aggcgtggcc gtcaaccaaa tgggcgagga atctatccg     960 caagcgctgg aggccaccat ccgcgaggcc tggcgcgttg ccggcatccc ggtgatggtc   1020
accgagaacg ggttggccac ggaggatgac acgcagcggg tggcgtacct gcggacggcc   1080
gtcgacggcg ttgcttcctg ccttgcggac ggcatcgacg tccgcgggta catcgcctgg   1140
accgcgttcg ataacttcga gtggatcttc ggctacgggc ccaagttcgg cctgatcgcc   1200
gtcgaccgtt caacccagga acggactccc aaggagagcg cgcgctggct gggcaacttc   1260
gcccggcagc aggcaccggc ggaggcaccg cagcccgcct ga                      1302
```

<210> SEQ ID NO 2
<211> LENGTH: 433
<212> TYPE: PRT
<213> ORGANISM: Artificial Sequence
<220> FEATURE:
<223> OTHER INFORMATION: Bgl3054

<400> SEQUENCE: 2

```
Gly Leu Gly Arg Arg Ala Ser Met Met Arg Gly Thr Pro Met Thr
 1               5                  10                  15

Asn Pro Phe Pro Gln Asp Phe Leu Trp Gly Val Ala Thr Ala Gly His
             20                  25                  30

Gln Val Glu Gly Asn Asn Val Asn Ser Asp Val Trp Phe Leu Glu His
         35                  40                  45

Leu Pro Gly Thr Ile Phe Ala Glu Pro Ser Gly Asp Ala Val Asp His
     50                  55                  60

Tyr His Arg Tyr Arg Glu Asp Ile Ala Leu Ile Ala Gly Leu Gly Phe
 65                  70                  75                  80

Thr Ser Tyr Arg Phe Ser Val Glu Trp Ala Arg Ile Glu Pro Glu Glu
                 85                  90                  95

Gly His Phe Ser Val Ala Ala Leu Asp His Tyr Lys Arg Val Leu Glu
            100                 105                 110

Ala Cys Arg Glu His Gly Leu Thr Pro Val Val Thr Phe His His Phe
        115                 120                 125

Ala Ser Pro Leu Trp Leu Leu Arg Ser Gly Trp Glu Gly Glu Arg
    130                 135                 140

Thr Pro Glu Leu Phe Ala Arg Tyr Cys Gly Arg Val Met Ala His Leu
145                 150                 155                 160

Gly Asp Leu Ile Gly Val Ala Cys Thr Leu Asn Glu Pro Asn Leu Pro
                165                 170                 175

Trp Leu Leu Glu Ser Phe Gly Ile Gly Gly Glu Ala Pro Glu Asn Arg
            180                 185                 190

Gly Lys Val Pro Met Trp Ala Ala Ala Gln Arg Leu Gly Val Asp
        195                 200                 205

Ala Ser Thr Val Ala Pro Phe Gln Phe Cys Ser Thr Glu Ala Gly Phe
    210                 215                 220
```

```
Asn Val Lys Leu Ala Ala His Lys Ala Ala Thr Glu Ala Ile Lys Ala
225                 230                 235                 240

His Arg Pro Asp Leu Arg Val Gly Trp Thr Leu Ala Asn Ser Asp Ile
            245                 250                 255

Gln Ser Val Pro Gly Glu Glu Ile Ala Ala Gln Val Arg Arg Asp
        260                 265                 270

Val Asn Glu Arg Phe Leu Glu Ala Ser Arg Gly Asp Asp Phe Val Gly
        275                 280                 285

Ile Gln Thr Tyr Gly Arg Thr Val Tyr Gly Pro Asp Gly His Ala Pro
290                 295                 300

Ala Pro Glu Gly Val Ala Val Asn Gln Met Gly Glu Glu Ile Tyr Pro
305                 310                 315                 320

Gln Ala Leu Glu Ala Thr Ile Arg Glu Ala Trp Arg Val Ala Gly Ile
            325                 330                 335

Pro Val Met Val Thr Glu Asn Gly Leu Ala Thr Glu Asp Asp Thr Gln
            340                 345                 350

Arg Val Ala Tyr Leu Arg Thr Ala Val Asp Gly Val Ala Ser Cys Leu
            355                 360                 365

Ala Asp Gly Ile Asp Val Arg Gly Tyr Ile Ala Trp Thr Ala Phe Asp
370                 375                 380

Asn Phe Glu Trp Ile Phe Gly Tyr Gly Pro Lys Phe Gly Leu Ile Ala
385                 390                 395                 400

Val Asp Arg Ser Thr Gln Glu Arg Thr Pro Lys Glu Ser Ala Arg Trp
            405                 410                 415

Leu Gly Asn Phe Ala Arg Gln Gln Ala Pro Ala Glu Ala Pro Gln Pro
            420                 425                 430

Ala

<210> SEQ ID NO 3
<211> LENGTH: 21
<212> TYPE: DNA
<213> ORGANISM: Artificial Sequence
<220> FEATURE:
<223> OTHER INFORMATION: primer for MUKAN-1 FP-1

<400> SEQUENCE: 3
ctggtccacc tacaacaaag g                                         21

<210> SEQ ID NO 4
<211> LENGTH: 22
<212> TYPE: DNA
<213> ORGANISM: Artificial Sequence
<220> FEATURE:
<223> OTHER INFORMATION: MUKAN-1 RP-1

<400> SEQUENCE: 4
agagattttg agacaggatc cg                                        22

<210> SEQ ID NO 5
<211> LENGTH: 29
<212> TYPE: DNA
<213> ORGANISM: Artificial Sequence
<220> FEATURE:
<223> OTHER INFORMATION: forward primer for pbgl3054-p1 DNA

<400> SEQUENCE: 5
cggatccaat gggcctggga cgccggcgt                                 29

<210> SEQ ID NO 6
```

```
<211> LENGTH: 27
<212> TYPE: DNA
<213> ORGANISM: Artificial Sequence
<220> FEATURE:
<223> OTHER INFORMATION: reverse primer for pbgl3054-p1 DNA

<400> SEQUENCE: 6
cggaagcttt caggcgggct gcggtgc                                            27
```